(12) United States Patent
Dehais et al.

(10) Patent No.: US 9,892,501 B2
(45) Date of Patent: Feb. 13, 2018

(54) ESTIMATION OF FOOD VOLUME AND CARBS

(71) Applicants: Roche Diabetes Care, Inc., Indianapolis, IN (US); University of Bern, Bern (CH)

(72) Inventors: Joachim Dehais, Paris (FR); Alan Greenburg, Indianapolis, IN (US); Sergey Shevchick, Zurich (CH); Abhishek Soni, Noblesville, IN (US); Marios Anthimpoulos, Bern (CH); Stavroula Mougiakakou, Bern (CH)

(73) Assignees: Roche Diabetes Care, Inc., Indianapolis, IN (US); University of Bern, Bern (CH)

( * ) Notice: Subject to any disclaimer, the term of this patent is extended or adjusted under 35 U.S.C. 154(b) by 100 days.

(21) Appl. No.: 14/978,433

(22) Filed: Dec. 22, 2015

(65) Prior Publication Data
US 2016/0163037 A1    Jun. 9, 2016

Related U.S. Application Data

(63) Continuation of application No. PCT/EP2014/063945, filed on Jul. 1, 2014.

(30) Foreign Application Priority Data

Jul. 2, 2013   (EP) ..................................... 13003338

(51) Int. Cl.
| | |
|---|---|
| *G06T 7/00* | (2017.01) |
| *G06K 9/62* | (2006.01) |
| *G06K 9/66* | (2006.01) |
| *G06T 7/521* | (2017.01) |

(52) U.S. Cl.
CPC .......... *G06T 7/0004* (2013.01); *G06K 9/6201* (2013.01); *G06K 9/6267* (2013.01);
(Continued)

(58) Field of Classification Search
CPC combination set(s) only.
See application file for complete search history.

(56) References Cited

U.S. PATENT DOCUMENTS

| | | |
|---|---|---|
| 7,742,640 B1 | 6/2010 | Carlson et al. |
| 8,233,668 B2 * | 7/2012 | Jing ...................... G06K 9/342 |
| | | 382/110 |

(Continued)

FOREIGN PATENT DOCUMENTS

EP    2161537 A2    3/2010

OTHER PUBLICATIONS

5hang, et al., Dietary Intake Assessment Using Integrated Sensors and Software, Proceedings of SPIE, vol. 8304, Feb. 1, 2012, pp. 830403-1-830403-11, USA (cited in IDS).*

(Continued)

*Primary Examiner* — Anand Bhatnagar
(74) *Attorney, Agent, or Firm* — Dinsmore & Shohl, LLP

(57) ABSTRACT

There is disclosed a system for estimating the volume of food on a plate, for example meal, with a mobile device. The system uses a camera and a light pattern projector. Images of the food with and without a projected light pattern on it enable to compute the tridimensional shape and volume, while image segmentation and recognition steps estimate one or more food types in said images. By applying accessible knowledge databases, the carbs content is estimated and the associated insulin bolus doses are provided. Developments comprise coding of the light pattern, different light sources and associated wavelengths, motion compensations, additional optics, estimation of fat content and associated multi-wave boluses. The invention can be implemented in a glucometer or in an insulin pump controller provided with a test strip port or with a mobile phone.

24 Claims, 13 Drawing Sheets

(52) U.S. Cl.
CPC ............... *G06K 9/66* (2013.01); *G06T 7/521* (2017.01); *G06T 2207/10024* (2013.01); *G06T 2207/30128* (2013.01)

(56) References Cited

U.S. PATENT DOCUMENTS

| | | | | |
|---|---|---|---|---|
| 8,345,930 | B2* | 1/2013 | Tamrakar | G06T 7/0002 382/110 |
| 9,254,099 | B2* | 2/2016 | Connor | A61B 5/1114 |
| 2005/0088643 | A1 | 4/2005 | Anderson | |
| 2006/0161380 | A1* | 7/2006 | Bottemiller | A22C 7/00 702/151 |
| 2010/0249530 | A1* | 9/2010 | Rankers | A61B 5/14532 600/300 |
| 2011/0182477 | A1* | 7/2011 | Tamrakar | G06T 7/0002 382/110 |
| 2012/0005222 | A1* | 1/2012 | Bhagwan | G06F 17/30389 707/769 |
| 2012/0170801 | A1* | 7/2012 | De Oliveira | G06K 9/6256 382/103 |
| 2013/0058566 | A1* | 3/2013 | Sato | G06K 9/4642 382/159 |
| 2014/0349256 | A1* | 11/2014 | Connor | G09B 19/0092 434/127 |
| 2016/0154823 | A1* | 6/2016 | Bhagwan | G06F 17/30389 382/110 |

OTHER PUBLICATIONS

Shang, et al., Dietary Intake Assessment Using Integrated Sensors and Software, Proceedings of SPIE, vol. 8304, Feb. 1, 2012, pp. 830403-1-830403-11, USA.

Strat, et al., An Inexpensive 3D Camera, ACM SIGGRAPH 2002 Sketches & Applications Program, Jul. 21, 2002, p. 146, USA.

Geng, Structured-Light 3D Surface Imaging: A Tutorial, Advances in Optics and Photonics, vol. 3, No. 2, Mar. 31, 2011, pp. 128-160, XP0855033088.

Salvi, et al., Pattern Codification Strategies in Structured Light Systems, Pattern Recognition, Elsevier, vol. 37, No. 4, Apr. 1, 2004, pp. 827-849, XP004491495, Great Britain.

Maimone, et al., Reducing Interference Between Multiple Structured Light Depth Sensors Using Motion, Department of Computer Science, University of North Carolina at Chapel Hill, IEEE Virtual Reality 2012, Mar. 4-8, pp. 51-54, USA.

Wireless Evolution, ETR Bulletin, Emerging Technologies Research (FBI Operational Technology Division), Mar. 1, 2011, pp. 1-84, XP055092829, URL:https://web.archive.org/web/20121020221911/http://fas.org/irp/eprint.

Kong et al., DietCam: Automatic Dietary Assessment With Mobile Camera Phones, Pervasive and Mobile computing, Elsevier, NL, vol. 8, No. 1, Jul. 18, 2011, pp. 147-163, XP028448045.

Written Opinion pertaining to Application No. PCT/EP2014/063945 with a filing date of Jul. 1, 2014.

* cited by examiner

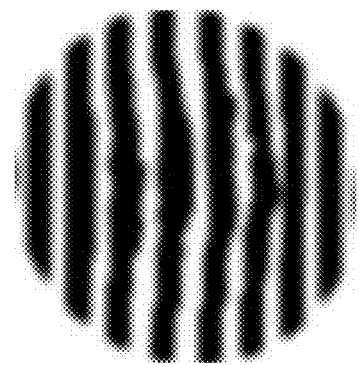 
FIG. 8A  FIG. 8B
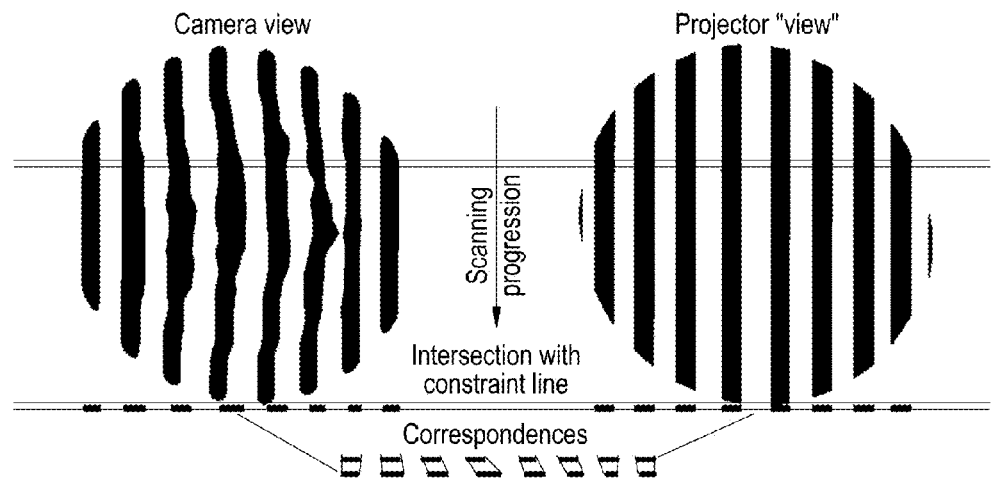
FIG. 9
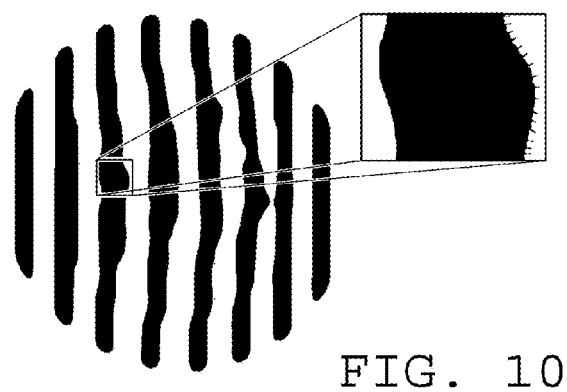
FIG. 10

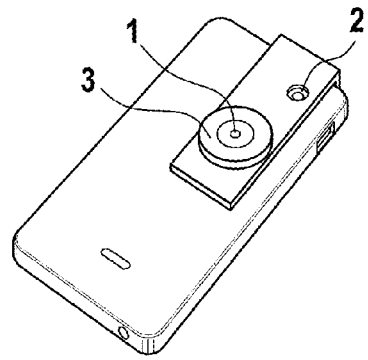
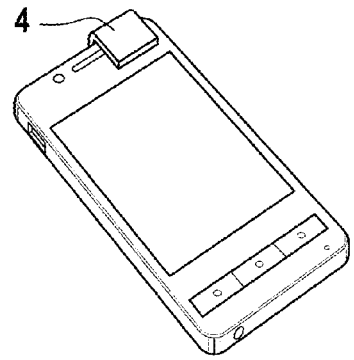
FIG. 16A    FIG. 16B
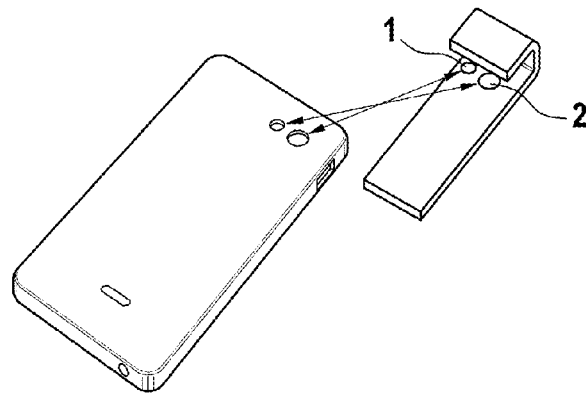
FIG. 16C
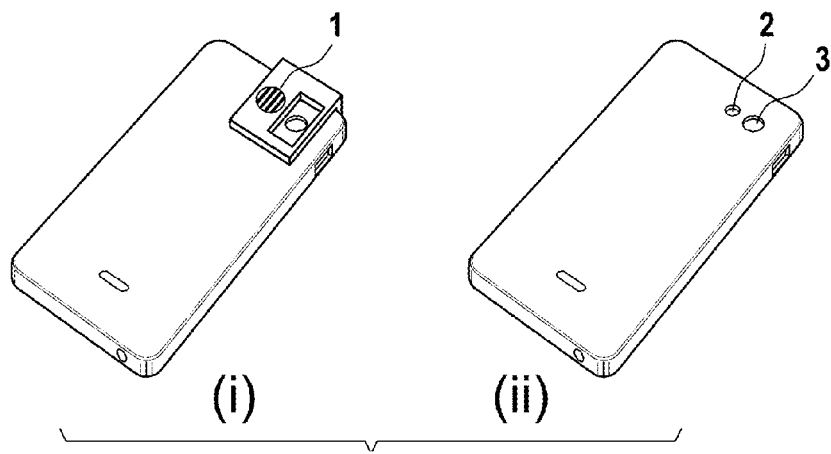
FIG. 16D

ESTIMATION OF FOOD VOLUME AND CARBS

CROSS-REFERENCE TO RELATED APPLICATIONS

This application is a continuation of PCT Application No. PCT/EP2014/063945, filed Jul. 1, 2014, which claims priority to EP Application Serial No. 13003338.4, filed Jul. 2, 2013, and which disclosures are incorporated herein fully by reference.

FIELD OF THE INVENTION

The present invention relates generally to methods, systems and devices for estimating the volume and carbohydrates (in the following referred to as carbs) content of food.

BACKGROUND OF THE INVENTION

Mobile phone associated applications represent a rapidly growing market that offers users a number of helpful tools for a wide variety of tasks. Recent achievements in hardware and signal processing have increased the usability of these tools and give users opportunities to carry out accurate measurements on their own.

In parallel, there is growing demand for portable devices suitable for self-assessment of diet with an especially strong need for patients with Diabetes Mellitus of type I. The total number of persons with Diabetes is estimated to 400 million, and this number will substantially increase in the next few decades. One of the critical tasks for persons with diabetes is the control of the amount and type of food intake. For them, diet affects glycaemia much more than for healthy individuals. Clinical studies have shown that for children and adolescents on intensive insulin therapy an inaccuracy of ±10 g in carbs counting does not deteriorate the postprandial control, while a ±20 g variation significantly impacts the postprandial glycaemia Food intake estimation is a non-trivial task due to a wide variety of food types and complex irregular shapes of servings. Image processing and computer vision techniques have made some progress, but numerous uncertainties remain and cumulate (recognition of the type of food, estimation of the volume, diverse lighting conditions etc). Regarding the estimation of volume, which is a key parameter, available 3D scanning techniques for industrial activities—using medium power consumption lasers to scan objects and reconstruct 3D shapes—are not adapted to mobile and personal environments. Industrial lasers require important sources of energy, may be dangerous for the eyes and may require several image acquisition devices.

The patent literature is developed for 3D or volume estimation in industrial environments, but scarce for mass-market type environments.

EP2161537 discloses a position measuring apparatus including a first irradiating part that irradiates a first beam to an object, a second irradiating part that irradiates a second beam to the object, a capturing part that captures images of the object, a processing part that generates a first difference image and a second difference image by processing the images captured by the capturing part, an extracting part that extracts a contour and a feature point of the object from the first difference image, a calculating part that calculates three-dimensional coordinates of a reflection point located on the object based on the second difference image, and a determining part that determines a position of the object by matching the contour, the feature point, and the three-dimensional coordinates with respect to predetermined modelled data of the object. This system presents drawbacks.

Shang et al: "Dietary intake assessment using integrated sensors and software", Proceedings of SPIE, Vol. 8304 page 830403, describes a system consisting of an mobile device that integrates a smartphone and an integrated laser package; software on the smartphone for data collection and laser control; an algorithm to process acquired data for food volume estimation, and a database and interface for data storage and management. The laser package creates a structured light pattern, in particular a laser grid.

The system collects videos with slow movement of the camera around the food, stabilized at several positions and collects video sequences. The laser is turned on and off during the video collection, resulting in video frames with and without laser grids alternatively. As the motion between two adjacent frames is considered small, the laser grid lines can be extracted by subtracting the non-grid images from the grid images.

Since the smartphone has only moderate computational power it is suitable for data collection but not for volume estimation. Therefore, acquired grid videos are transferred to a server for further processing. Furthermore, the food types are manually identified by the user, while the selection of several pairs of images whose motion is small is performed manually too. Those limit the system's usability.

There is a need for methods, systems and portable devices of estimating volume of objects (e.g. food) and to derive food nutritional values and insulin bolus advice thereof.

SUMMARY OF THE INVENTION

The present invention is related to applications for camera-enabled portable devices (e.g. mobile phones, smartphones) to be used for food volume estimation using structured light, for food segmentation/recognition by image analysis and for advanced bolus suggestion features. Using the combination of data analysis/processing and variations in surface highlighting, 3D scanning principles are adapted to mobile devices such as mobile phones, which present particular image acquisition conditions. Examples teach how to filter noise and signal artifacts. Embodiments of the invention solve technical problems including these of miniaturizing of light source to make it possible to use as an attachable device, optimizing processing algorithms to fit in the constraints of calculation power on the mobile devices and achieving effective noise reduction.

This is achieved by an inventive system as described in claim 1.

There is disclosed a system for estimating the volume of an object, said system comprising instructions which when performed by a processor result in operations comprising: receiving a first image of the object from an image acquisition component; projecting a light pattern on the surface of the object with a light pattern projection component; receiving a second image of the object being highlighted with said light pattern from the image acquisition component; subtracting the first and second images; identifying the projected light pattern on the object; and computing the tridimensional shape and the volume of the object given the deformations of the projected light pattern.

In an optional development, the irradiation power of the light pattern projection component can be inferior to 5 mW. For ambient lightning conditions, a suitable irradiation power can be superior to 0.5 mW. In a development, the light pattern projection component comprises one or more light sources chosen from the list comprising a low intensity semiconductor LASER diode, a LED, an organic LED (OLED), a pre-existing mobile phone flash such as a white LED or a miniaturized halogen lamp or a combination thereof. More preferably the light source is operated in continuously mode or in impulse mode with pulse frequencies between around 0.1 to 100 Hz even more preferably between 0.5 and 10 Hz.

In a particular embodiment the power consumption of the light source is less than 0.7 W, in particular the power consumption is in range between around 0.05 W and around 0.7 W.

In a development, the system in particular the light pattern projection component comprises an optical objective adapted to form and project and/or to focus the light pattern onto the object. Preferably the optical objective has an irradiation loss inferior to 60% from the total output of the irradiation power of the light source.

In a development, the relative pose and orientation of the light pattern projection component and the image acquisition component is static or invariant during the image acquisition operation and/or the light pattern projection operation. In a development, the projected light pattern is composed of geometrical motifs such as sequences of stripes, or dots, or repetitive graphical elements or of a combination thereof. In particular the geometrical motifs have a bright area the power density at which is inferior to 55 mWt/cm$^2$.

In a development, the light pattern is coded by color and/or phase and/or amplitude modulation. In a development, the coding of the light pattern is predefined and is synchronized with the image acquisition component. The total irradiation power for all color components is equal or inferior to the output irradiation of the light source of the light pattern projection component.

In a development, the coding can be achieved by matching the spectra of the one or more sources to the maxima transfer rates of the filter of the image acquisition component. In a development, the system further comprises an operation of correcting the first and/or the second image by compensating the movements of the image acquisition component during the image acquisition operation. In a further development, the compensation is performed by processing data received from an accelerometer and/or a gyroscope and/or a motion sensor and/or a mechanical optical component and/or an electrical optical component and/or a camera tracking device and/or a magnetometer and/or a computer vision tracking device associated with the mobile device.

In a development, the compensation is performed by multi-view geometry methods (e.g. pose solvers using image features) or projective warping or by piecewise linear, projective, or higher order warping, or by deconvolution or by oriented image sharpening or by optical flow detection before or after or in an iterative refinement process with the subtraction of the images. In a development, the object is food and further comprising the operation of performing food recognition of the first and/or the second image to estimate one or more food types in said image and one or more volumes associated with said food types. In a development, the food recognition operation comprises one or more of the operations of segmenting the image, identifying color and/or texture features of segmented parts of the image and performing machine learning based classification for one or more segmented parts of the image or a combination thereof.

In a development, the system further comprises an operation of estimating one or more nutritional characteristics of the meal captured in the first or second image by multiplying the estimated volumes of the determined food types by unitary volumetric values retrieved from a database, said database stored remotely (e.g. cluster, server and/or computer network) and being accessed through any available wired and wireless communication channel and/or stored locally on the device, and/or determined from food labels by using optical character recognition (OCR) and/or associated with geolocation data and/or provided by the user. In a further development, the one or more characteristics, of the meal or of parts thereof, are one or more of carbs content, fat content, protein content, Glycemic Index (GI), Glycemic Load (GL) and/or Insulin Index (II) or a combination thereof. In a development, there is provided an insulin dose recommendation and/or a bolus profile advice based on said one or more meal characteristics. In a development, the projection of the light pattern and in particular the whole pipeline performed by the system, is triggered by voice command or by gesture command and/or by touchscreen command and/or keyboards and/or by geofencing and/or geo positioning and/or by following a predefined time schedule. In a development, the image acquisition component and the light pattern projection component are embedded in a mobile device such as a glucometer or an insulin pump controller provided with a test strip port or a mobile phone.

In a development, the light pattern projection component is attachable to the mobile device. Preferably the light pattern projection component is inserted i.e. connected to an electrical contact slot of the system, in particular such as a charge slot or an USB slot preferably of a handheld device e.g. preferably a smart phone.

In a development, the first or the second image is a video frame and the image acquisition component is a video camera.

In a development, one or more operations are continuously, and in particular automatically, repeated until the acquisition of the first and/or the second image is considered as sufficient based on predefined thresholds associated with criteria comprising one or more of image quality, associated measurements of handshakes, time delays between still images or video frames, resulting light pattern or a combination thereof.

In a further embodiment the image acquisition component has sensitivity inferior to 5 lux.

There is disclosed a computer program comprising instructions for carrying out one or more of the operations according to the present disclosure when said computer program is executed on one or more suitable components. There is also disclosed a computer readable medium having encoded thereon such a computer program.

BRIEF DESCRIPTION OF THE DRAWINGS

FIGS. 8A and 8B illustrate examples of binarisation;

FIG. 9 shows the matching process between the edges of corresponding stripes on camera view and projector view;

FIG. 10 shows a curve tracking for consistent matches;

FIGS. 16A, 16B, 16C, 16D and FIGS. 17A, 17B illustrate the various options of implementation in mobile devices (e.g. mobile phones, glucometers, insulin pump controllers), as extensions or accessories or as natively embedded components.

DETAILED DESCRIPTION

There is disclosed a system for estimating the volume of a food, with a mobile device. The system uses a camera and a light pattern projector. Images of the food with and without a projected light pattern on it enable to compute the tridimensional shape, image segmentation and recognition steps identify and recognise one or more food types in said images, while the volumes are computed by using the shape and the segmentation and recognition results. By applying offline or remotely accessible databases, one or more carbs values are estimated and one or more associated insulin bolus doses are provided. Developments comprise coding of the light pattern, different light sources and associated spectral properties, motion compensations, additional optics, estimation of fat content and associated multi-wave boluses. The invention can be, e.g. implemented in a glucometer or an insulin pump controller provided with a test strip port or a mobile phone.

There is disclosed a device attached or embedded into a mobile phone for retrieval of the three-dimensional structure of surfaces, composed of the external miniature unit to generate and/or project low intensity light pattern or patterns on the surface and data processing algorithm. The device is placed on or in a mobile phone at a predetermined position, and controlled by the mobile phone. As a control channel a Bluetooth, phone jack or mobile phone flash can be used. The control is carried out by dedicated software application. The mobile phone software takes two photographs of the object sequentially with and without pattern highlighting. Pattern is extracted using the resulting subtraction of images. Further the 3D shape of the surface and the associated volume are computed. In order to estimate the carbs content the computed shape, along with the results of automatic or semi-automatic food segmentation and recognition, and nutritional databases are used.

Figure 1A:
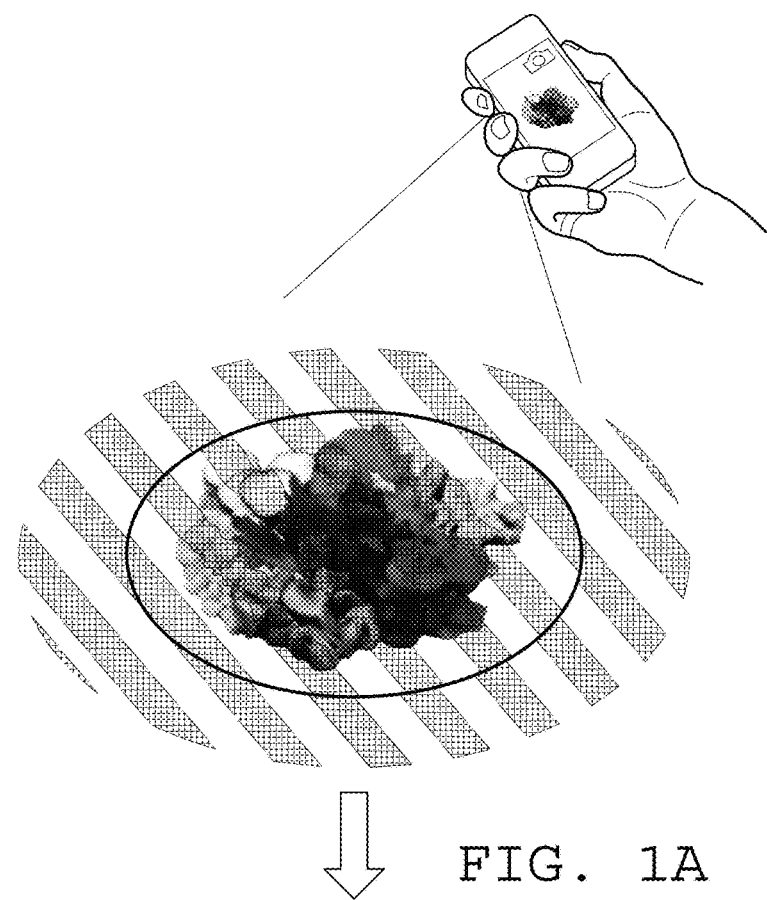
FIGS. 1A and 1B illustrate the practical use of embodiments of the method.
Figure 1B:
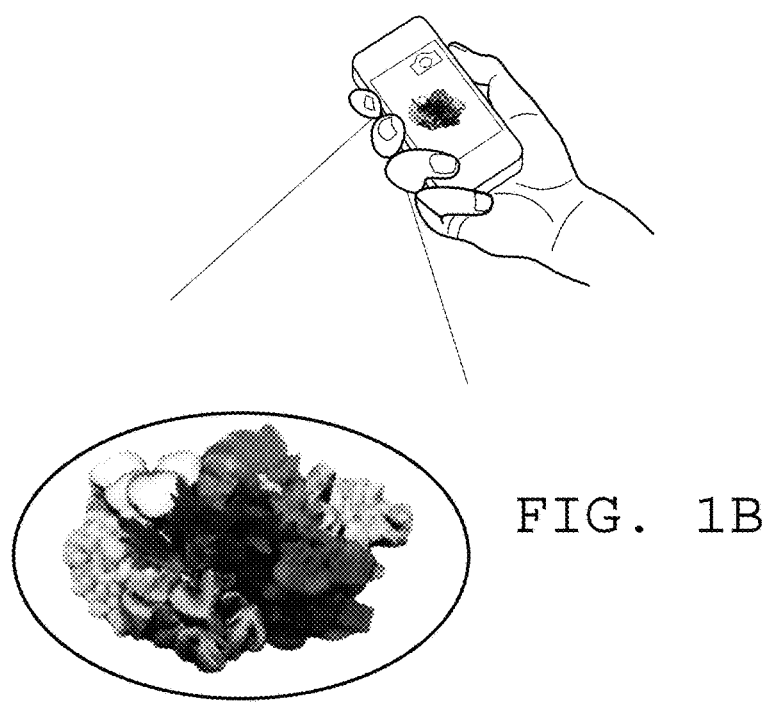

FIGS. 1A and 1B illustrate an example of a practical use of the method, when some particular embodiments are implemented. The device according to the invention (comprising one or more image or video acquisition means and one or more projector means) is attached to the mobile phone. Alternatively, such a device is embedded in the mobile phone. In the case wherein the device is attached to the mobile phone in a fixed position, the orientation of light patterns is predefined and allows the use of simplified algorithms on mobile phones. The dedicated application can be launched on the mobile phone by the user. The mobile phone is then placed in some position oriented towards the dish. The user launches the measurements with a virtual control on the display for example (e.g. pressing a button or activating a touch screen area). The application ("app") triggers successive sub-steps. It first turns on the irradiation (projection of the light source). Optionally the triggering can be achieved by turning on the mobile phone flash. The triggering also can be achieved by a command transferred to the device via Bluetooth or phone jack. The optical objective of the device forms a light source beam into a specific pattern. The shape of the pattern can be predefined (or adaptive, when successive illuminations occur for example). The projection of the light pattern covers all the field of view of the mobile phone camera. One picture shot (image acquisition) is carried out. The application then switches off the illumination and repeats the shot without highlighting. The application then distinguishes the different food elements present in the dish, computes the different volumes and the different associated food categories. In the end, the application proposes one or more bolus values to the user. In some embodiments, the segmented image is shown indicating the different recognized parts and the associated carbs values. In some further embodiments, the fat content and other nutritional values are estimated as well and a multi-wave bolus can be proposed, to match the kinetics of blood sugar rise with the insulin effect in the body.

In some embodiments, the position of the mobile device can be adjusted using the screen operating as a view finder, with guarantee of highlighting the chosen field of view with the light pattern. In other words, by principle the view finder focus the camera on the right object, the field of view of the optics being designed to cover the field of view of the camera.

In some embodiments, steps of the method are performed before the consumption of the meal and repeated after the meal is consumed. By subtracting estimated volumes, further carbs estimation can be conducted. It may well be indeed that the user does not eat the meal completely and in such a case, subtractions operations would have to be performed. Since the food plate can be segmented into several parts (corresponding to different food categories e.g. steak and potatoes), there can be associated estimations of several volumes and following a global insulin bolus recommendation can be proposed, or several bolus values each associated with the different food parts, said insulin dose or doses corresponding to food actually consumed.

Figure 2:
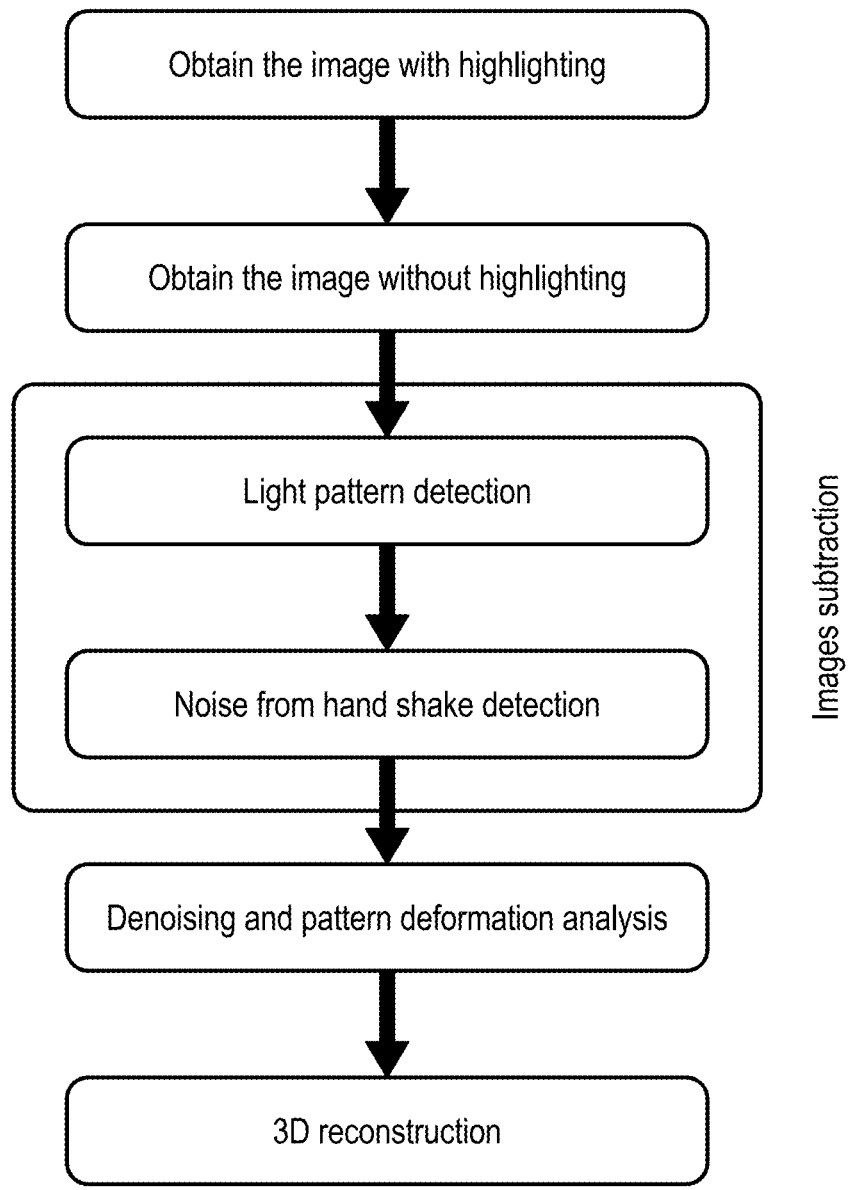
FIG. 2 is a schematic and exemplary workflow of the method of volume estimation.

FIG. 2 is a schematic and exemplary workflow of the method of volume estimation. The preinstalled application ("app" or program) on the mobile device comprises a user interface, to allow the user to interact with the system e.g. to start or to stop the measurements. The user keeps the mobile phone at a fixed position above the object of interest (e.g. food on a plate). Then, the application obtains automatically two shots of the object within a minimal timeframe. After the image acquisition, the program extracts the pattern using the two acquired images. This is performed by subtraction of the image which contains light pattern from the simple image without light pattern. The result of the subtraction is used to obtain the light pattern and its shape. Before or after or in an iterative process with the subtraction and light pattern detection, the artifacts that are induced by user hand shake are detected and corrected. Handshake generates motion blur, which can be formulated as a convolution kernel, this kernel may be automatically detected and then automatically compensated by using image denoising. Furthermore, multi-view approaches allow detecting the motion by using common features on the image sequence; computing the relative pose and orientation. Alternatively, general projective and image warping transforms can be applied using common points between the images, and thus used to map one image onto the other, removing artifacts due to motion. Optical flow is a dense equivalent of image warping, which may find a more optimal transform, and provide more accurate error compensation. Once the motion is detected it is corrected by image remapping.

Several methods can be used for 3D reconstruction.

For example the 3D reconstruction from light patterns can be performed by computing deformations of individual lines. The gradient also can be counted running along each line and the depth of the scene can be computed by triangulation. Triangulation consists in using the known triangular connectivity of projecting points on multiple cameras to retrieve their position in space. Considering the projective geometry of points in space, the projection of a point in space is on the straight line joining this point and the camera center. When in presence of a plurality of cameras, the segments joining a point to two cameras and the segment joining the two camera centers form a triangle and the projections of the point are on the two segments joining point and camera. Said triangulation uses the projections of a point to reconstruct the corresponding triangle, where the third corner is the point in the 3D scene. This step is applied to all correspondences between images. A cloud of point is obtained, representing the scene depicted in the images. The identification of the corresponding projections of points in the different images, called <<point correspondences>>, is facilitated by the use of the projected light pattern according to different embodiments of the invention. For example, using stripe patterns, finding point correspondences in multiple images is simplified compared to the task of finding corresponding stripes in multiple images. A single reference stripe is necessary to obtain matches for all points, by propagating stripe indices away from the reference ('horizontally') in both images simultaneously. By propagating the indices along stripes ('vertically'), gradual occlusions within stripes can be handled. The step of propagating horizontally increases the stripe index every time a black and white boundary is crossed. The step of propagating stripes indices vertically keeps the same index for the points in a connected component. By choosing the minimum propagated index at each point, the right stripe matching is obtained (unless there is a collection of large objects in the foreground occulting the objects of interest but in practice this does not happen when scanning food or similarly when scanning simple scenes on a flat plane).

Figure 3A:
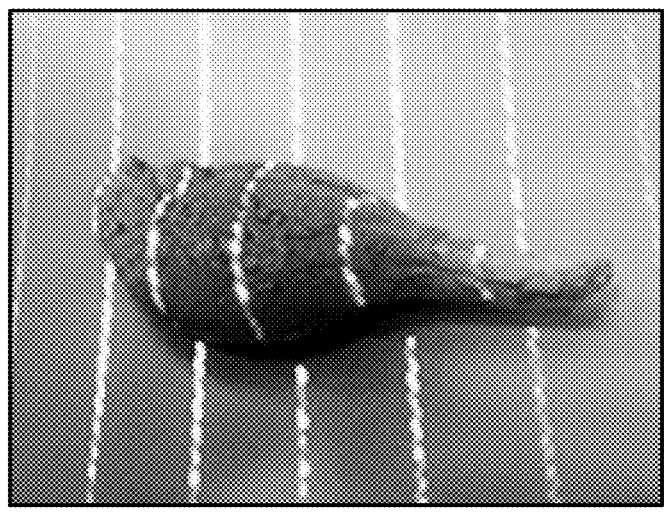
FIGS. 3A, 3B and 3C show examples of an analyzed object, with and without a light pattern projected on it, the resulting identification of the light pattern and the detected handshake movement.
Figure 3B:
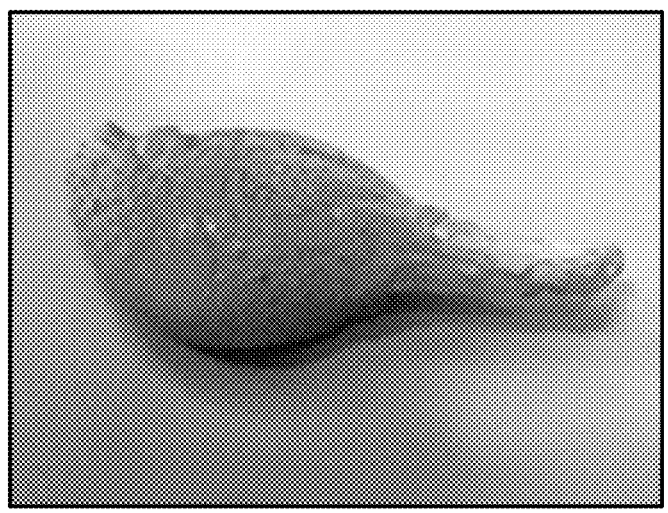
Figure 3C:
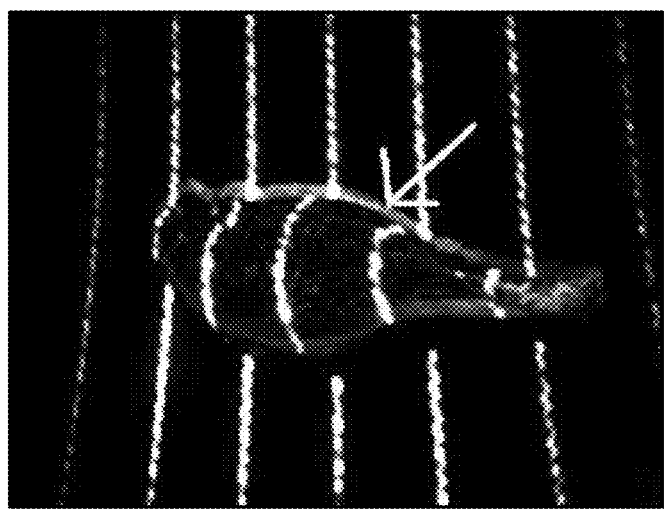

FIGS. 3A-3C show examples of an analyzed object, with and without a light pattern projected on it, the resulting identification of the light pattern and the detected handshake movement. FIG. 3A shows the object (e.g. chicken wing) with the light pattern projected on it (i.e. the bright stripes). FIG. 3B shows the object without highlighting. FIG. 3C represents the result of the subtraction between the two images, resulting in the identification of the light pattern. The movement of camera can be observed due to the hand shake (marked on the image by an arrow).

Figure 4A:
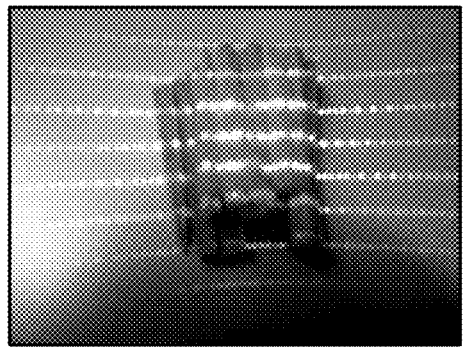
FIGS. 4A, 4B, 4C, 4D and 4E show examples of the steps of 3D reconstruction.
Figure 4B:
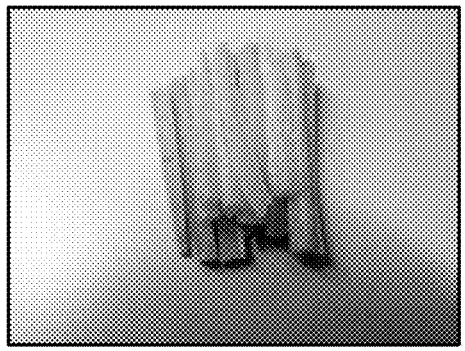
Figure 4C:
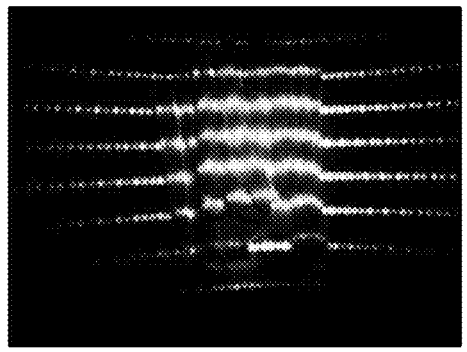
Figure 4D:
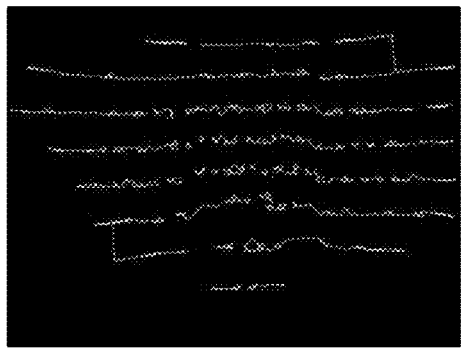
Figure 4E:
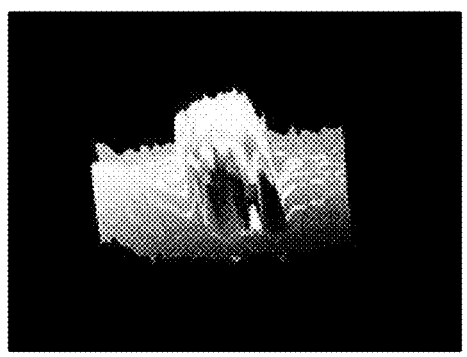
Figure 5A:
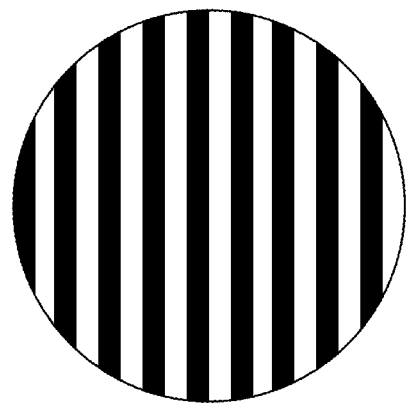
FIGS. 5A, 5B, 5C and 5D shows some possible variations of the light pattern structure.
Figure 5B:
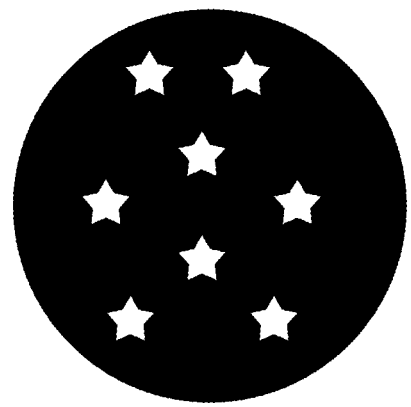
Figure 5C:
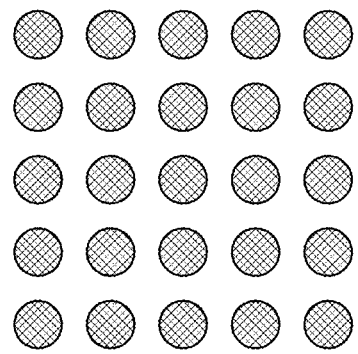
Figure 5D:
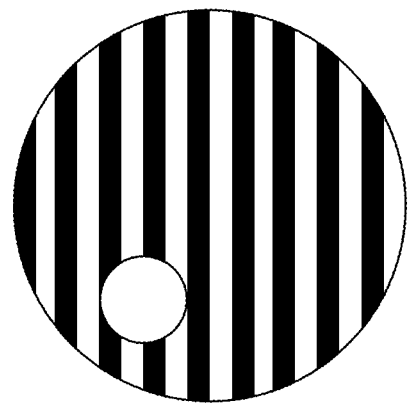

FIGS. 4A-4E show examples of the steps of 3D reconstruction, including the subtraction of images, the noise removal step and the 3D shape computation steps. FIG. 4A and FIG. 4B show the test images with and without light pattern. FIG. 4C shows the subtraction result of the original images (A) and (B) without "hand shake". FIG. 4D shows the processing of light patterns and making them 1 pixel thin. FIG. 4E shows the 3D model computed from the deformation of lines.

FIGS. 5A-5D show some possible variations of the light pattern structure, which are examples only. The shape of the elements of the pattern can give the information about the distance to the object, as far as its deformation about the local depth. The light patterns can be obtained from the light sources directly, from replaceable or predefined masks in or non-optical elements in the device attached to the mobile or natively embedded in the mobile device. For example, the mobile phone flash can contain an optical element, amplitude zone plate that forms the light pattern. The structure of the pattern can vary as shown by some examples in (FIG. 5A) stripes, (FIG. 5B) repetitive elements, (FIG. 5C) dots or even (FIG. 5D) mixtures thereof.

The 3D information extraction according to the present method is simplified over techniques analysing the reflection of light patterns on analysed surfaces. In a preferred embodiment, the 3D information is obtained by encoding the surface using static light patterns. Still, according to some further developments of the present methods, it can be possible to move or rotate the light pattern(s) during image/video acquisition (acquiring more images for example) which additional steps may enable to save binary information on stripes of the surface (and following to deduce information on the texture and nature of the parts of the surface being analysed).

Figure 6:
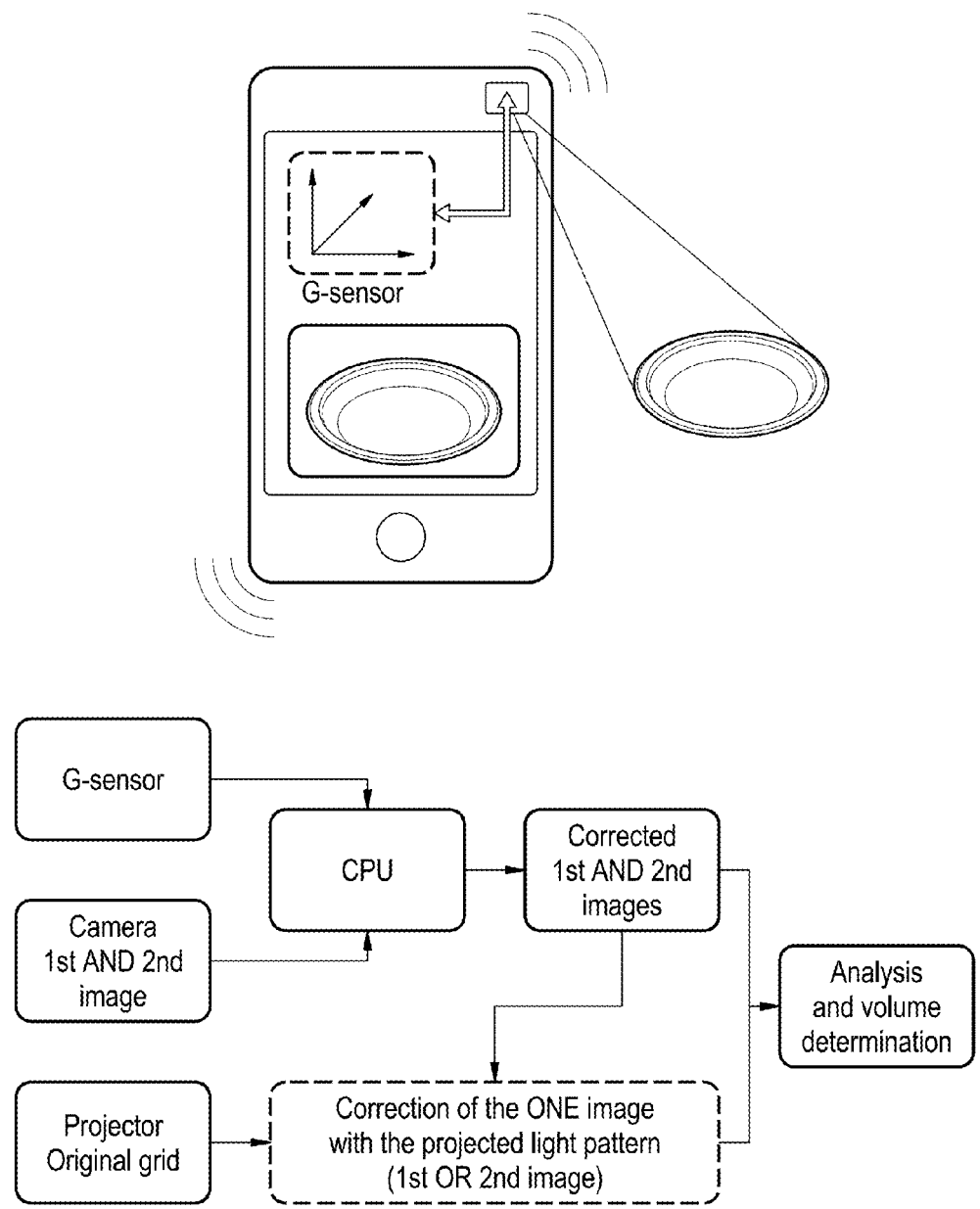
FIG. 6 illustrates the handshakes compensation system.

FIG. 6 illustrates the handshakes compensation system. While a fixed camera (i.e. with stable conditions in space during image acquisition) leads to accurate volume measurements, some embodiments of the invention enable image acquisition in a mobility situation (i.e. with relatively unstable conditions in space during image acquisition). When the mobile device is held by a person, the hand of the user can shake while image acquisition is performed (while obtaining the snapshots of the surface).

According to some embodiments of the invention, the detected movements of the device due to handshakes can be taken into account in order to compensate these movements and in fine to reduce noise artifacts. The described method advantageously leverages the accelerometer and/or motion sensor data measured and available in and for the device. The method therefore can go beyond the handling of pure pattern lines extraction, by taking into account compensation data, namely artifacts generated by the handshake. As a result, the accuracy of the volume is increased. Without compensation, the artifact lines due to handshakes would otherwise participate in less accurate (but still valuable) three-dimensional reconstruction.

Various mechanisms or components can be used to compensate handshakes: motion sensors (for example accelerometer or gyroscope), mechanical (and/or electrical) optical elements for image stabilization. In a preferred embodiment, the existing optical elements of a mobile phone are used and handshakes are compensated by software corrections on the basis of accelerometer or motion sensor data. An accelerometer is a device that measures proper acceleration. Single- and multi-axis, e.g. 3-axis, models of accelerometer are available to detect magnitude and direction of the proper acceleration (or g-force), as a vector quantity, and can be used to sense orientation (because direction of weight changes), coordinate acceleration (so long as it produces g-force or a change in g-force), vibration, shock, and falling in a resistive medium (a case where the proper acceleration changes, since it starts at zero, then increases). Micro machined accelerometers are increasingly present in portable electronic devices and video game controllers, to detect the position of the device or provide for game input. In commercial devices, piezoelectric, piezo-resistive and capacitive components are commonly used to convert the mechanical motion into an electrical signal. An accelerometer and/or a gyroscope can be used to compensate handshakes. An accelerometer alone can be used. A gyroscope alone can be used. A combination of an accelerometer with a gyroscope can be used. A gyroscope allows the calculation of orientation and rotation. Such components have been introduced into consumer electronics and are readily available in devices. The integration of the gyroscope has allowed for more accurate recognition of movement within a 3D space than the previous lone accelerometer within a number of smartphones. Gyroscopes in consumer electronics are frequently combined with accelerometers (acceleration sensors) for more robust direction- and motion-sensing. Other mechanisms can be used: camera tracking, magnetometers, position tracking by computer vision.

In addition, one or more additional optical elements can be used to correct handshakes or vibrations. Some noise cancelling sensors may be used indeed. For example, further additional light pattern(s) can be introduced, and their deformed dimensions and/or intensity of reflected light further analysed. Such additional optical elements can be implemented natively in a specific mobile device, e.g. in the remote control of an insulin pump, or can be implemented through an extension device to be connected to a standard mobile phone or remote control. Electromechanical optical arrangements can also be used to compensate for pan and tilt (angular movement, equivalent to yaw and pitch) of a camera or other imaging device. It is used in image-stabilized binoculars, still and video cameras, and astronomical telescopes. With still cameras, camera shake is particularly problematic at slow shutter speeds (in the dark).

With video cameras, camera shake causes visible frame-to-frame jitter in the recorded video. In video embodiments, real-time digital image stabilization can be used, by shifting the electronic image from frame to frame of video, enough to counteract the motion. Such a technique uses pixels outside the border of the visible frame to provide a buffer for the motion. This technique reduces distracting vibrations from videos or improves still image quality by allowing one to increase the exposure time without blurring the image. This technique does not affect the noise level of the image, except in the extreme borders when the image is extrapolated.

Further embodiments for handshake compensation are now discussed. According to another embodiment, handshake and/or hand movements during measurement can be approximated by a homography (a projective transformation from one image to the other). When changing the point of view in a 3D scene, image deformations of objects are projective for planes and non-projective for all non-planar objects. However, if the movement of the camera is small, non-projective transformation in the image are also small in amplitude and can be approximated by projective transformations. Furthermore, the requirement is not an exact match between pixels but a near-exact match in colors and neighborhoods.

In another embodiment, image warping is used for correcting shakes between images. Warping is done by finding sparse pixel correspondences between two images, tessellating the images (triangulation, quadrangulation, etc.), and applying local transformations to each element to map them to their corresponding element in the second image.

In another embodiment, the image features are extracted from the acquired images, the correspondences between features are estimated and used to compute the relative camera poses before and after the handshake (with 5-, 7- or 8-point algorithm). Once all the images are rectified, transformations (e.g. shift, rotation, zoom) are applied to the rectified images to fit each element from one image to the corresponding element of the other.

In another embodiment, optical flow is used. In such a development, each pixel in one image is mapped to the corresponding pixel in another image. The motion can be detected using global methods (phase correlation approach) or local (e.g. sum of squared differences, sum of absolute differences) or with differential methods (Lucas-Kanade, Horn-Schunk methods etc).

In another embodiment, one or more steps of de-blurring are applied. For example, inverse convolution with a linear shift invariant filter is applied to an image to increase details. The choice of the one or more filters depends on the application. In a preferred embodiment, the filter can be made of spatial translation (motion blur) and of a randomized component (shake).

It is to be noted that these methods of compensations can be combined and they leverage or benefit from the existing internal hardware of mobile phones. For example, the path (in space) taken by the mobile phone during the course of the measurement is a linear multiple of time plus the double integral of accelerometer measurements over time. The series of gyroscopic measurements indicates the orientation of the device at all points in time. Such information can allow the computation of the change in viewpoint. This in turn facilitates the application of the different embodiments or methods previously described.

$\Delta P$, the difference in positions, is defined as:

$$\Delta P(t_1,t_0)=(v(t_0)*(t_1-t_0)+\iint_{t_0}^{t_1} a(t)\delta t^2)$$

Where:

$v(t_0)$ is the original speed of the device, it is unknown and assumed to be 0, $a(t)$ is the acceleration vector at a given time, it can be obtained from inbuilt accelerometers $t_1-t_0$ is the time between two image-captures as can be obtained from the system clock.

Orientation can be obtained by:

gyroscopic measurements, if available;

integrating rotational accelerations from accelerometer data.

This data can be retrieved from 3 distinct accelerometer data streams, and the knowledge of their placement in the device.

Figure 7A:
FIGS. 7A and 7B illustrate the method of extracting the light pattern from successive images.
Figure 7B:
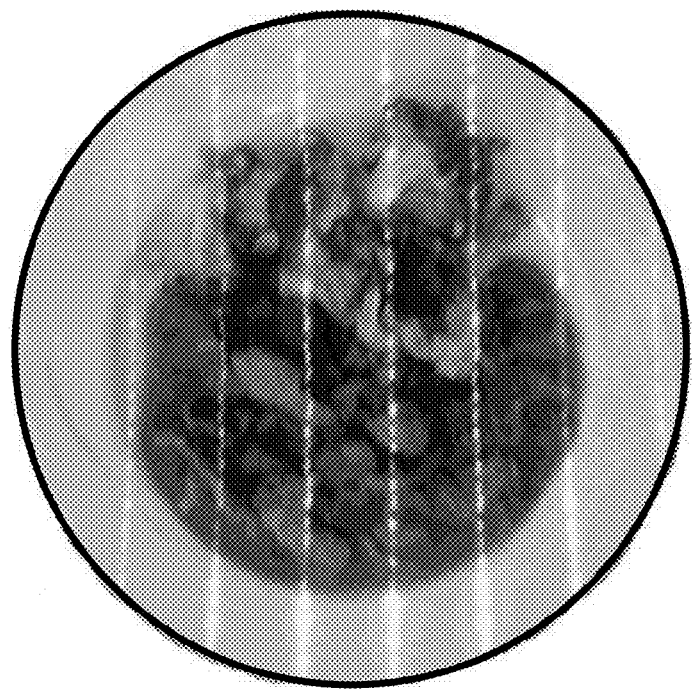

FIGS. 7A and 7B illustrate the method of extracting the light pattern from successive images. The figure shows the image acquisition procedure which consists of a sequence of acquisition of two images (A) one highlighted with a light pattern, and (B) one normal, i.e. without the projected light pattern. On FIG. 7A, the external light source is attached to a mobile phone device (or is an integral part thereof). It generates a coded light pattern. The pattern is projected on the investigated surface (in the present case on served food). Coding can be performed by spatial, phase and/or amplitude modulation, i.e. intensity or colour change. The highlighted area should at least correspond to mobile phone camera field of view (FOV). This requirement implies that the pattern safely covers the object of interest and partly covers the area of the table around it. The user then launches the specialised application (pre)installed on his/her mobile phone and holds the phone in a position and angle that ensure that the entire meal is within the camera's FOV, e.g. the mobile phone can be placed parallel to the table, at a distance of about 30 cm. The application triggers the external light source (pattern projector) via the mobile phone flash, Bluetooth, phone jack etc. An image of the dish highlighted by the pattern is acquired. On FIG. 7B, the application turns off the external light source and another picture is taken. The two images can be acquired with minimum delay, in order minimize camera shake and motions blur. Motion correction can be performed using deconvolution methods (computational expensive) or oriented image sharpening.

Once image acquisition is completed, a high contrast image of the light pattern is extracted. This operation is achieved by using pixel-wise subtraction of the two images:

$$I_{sub}(x,y)=I_{lp}(x,y)-I(x,y)$$

where x and y are the coordinates of pixels, $I_{sub}(x,y)$ is the resultant intensity at coordinates (x,y). $I_{lp}(x,y)$ and $I(x,y)$ correspond to the colour intensities of pixels in the image that contains the light pattern and the image without the light pattern. Subtraction can be performed for all colour channels, or only for one if laser source wavelength is known and unique. Next step is edge detection using binarisation and/or other methods.

FIGS. 8A and 8B show examples of binarisation: FIG. 8A shows noisy captured stripe pattern and FIG. 8B shows the resulting binary flags after threshold selection (black—0, white—1). To reinforce the edges in $I_{sub}$ before detection, several methods can be applied, e.g. simple binarisation (conversion to black-white) of $I_{sub}$ given a fixed threshold:

$$I_{bin}(x, y) = \begin{cases} 1, & \text{if } I_{sub}(x, y) > \text{threshhold} \\ 0, & \text{if } I_{sub}(x, y) \le \text{threshold} \end{cases}$$

where $I_{bin}(x,y)$ is the binary value of the pixel with coordinates x and y. The result of such an operation is the reflected light pattern (FIG. 8B). Threshold value can be determined adaptively from statistical analysis of the image (mean, median, histogram search). Pixel jitter can be removed by selecting the modal binary flag over a small neighborhood (no more than a stripe's width). Edges are extracted from a binary image by keeping only pixels of one flag with a direct neighbour of another flag (e.g. black pixel with white neighbour or white pixel with black neighbour). Without binarisation, edges are extracted using the Canny or Sobel operators, phase coherence methods, or wavelets.

Coding of the light pattern is now discussed.

In a development, amplitude and phase modulation of the highlighting irradiation can be used, in order to achieve better recognition of light patterns on the images.

In embodiments where the light pattern is coded, two further developments can be used. The first is to use Bruijn code (color coding the stripes) and the second one is to use time coding. Polarization, phase modulation and amplitude modulation also can be used. These developments allow the minimization of occlusions that may appear in image acquisitions. They can be used in combination.

FIG. 9 shows the matching process between the edges of corresponding stripes on camera view and projector view in a parallel stereo setup. The resulted image (camera view) is scanned by a vertically-moving horizontal line. In addition, FIG. 9 presents the correspondences between the camera and the projector views which are detected.

FIG. 10 shows an optional step of curve tracking for consistent matches. Follow the (oriented) normal to the gradient (or go through connected neighborhoods) to reconstruct the curve. Consistent matching can be obtained by tracking the curves from one end of the image to the other. Alternatively, a propagation method can be used.

Figure 11A:
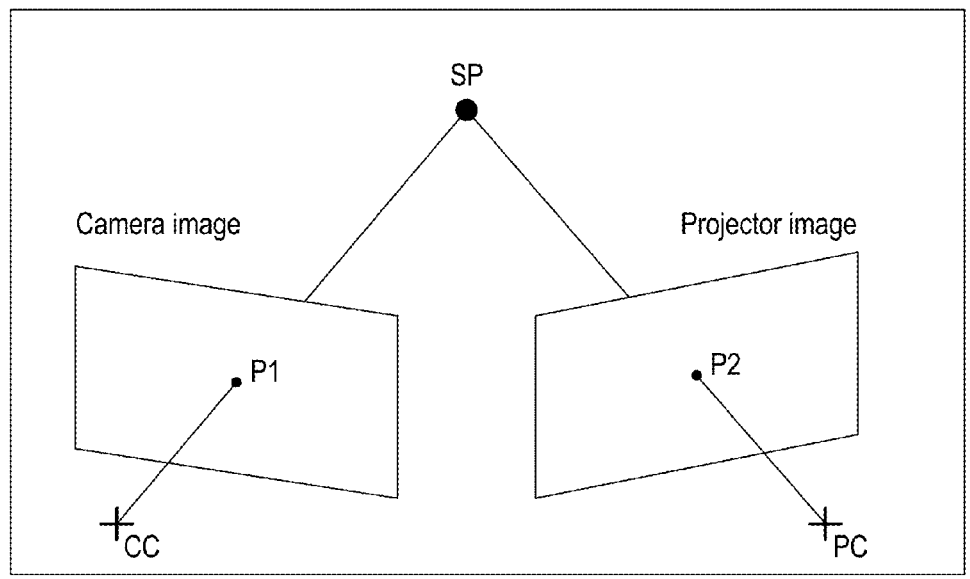
FIGS. 11A and 11B illustrate the image acquisition process.
Figure 11B:
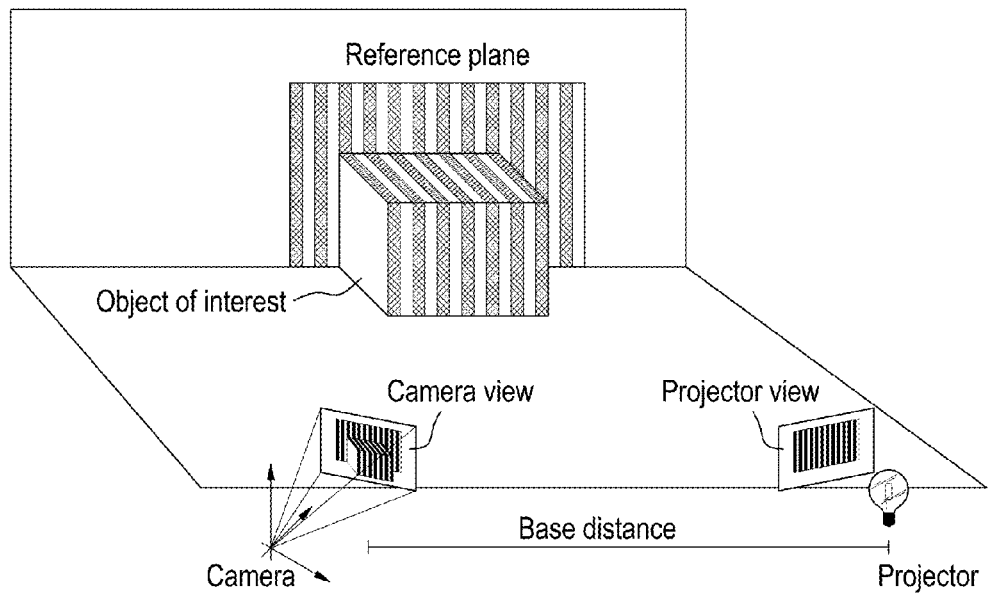

FIGS. 11A and 11B illustrate the design of the structured light setup comprised by an imaging sensor (camera), a structured-light projector and the object of interest. A light pattern is projected (via the projector) to the object of interest, while the camera acquires the corresponding object image (highlighted by the projected pattern). Depth information can be obtained by measuring the distortion between the captured image and the reflected image. The most simple and commonly used pattern is a sequence of stripes, while other coded light patterns are applicable. It has to be noted that the proposed solution refers to a system of known camera-projector configuration. FIG. 11A shows the depth estimation of a 3D scene point (SP) knowing the projections in each image (P1 and P2), as well as the centers of the camera (CC) and the projector (PC). Knowing the system configuration (relative translation and orientation between camera and projector, internal projector parameters and internal camera parameters), as well as the already detected correspondences, the depth/relative position of a 3D point (SP) can be estimated. Specifically: i) The detected correspondences specify the projections of the 3D points to each of the images (P1, P2); ii) the projection of the SP to the Camera image is in the line joining the point and the camera center (CC). The same applies to the projection of the 3D point to the Projector image. Those two lines intersect by definition to SP; iii) knowing the CC and PC, as well as the two projections of the 3D point (P1 and P2), the depth of the SP can be estimated.

According to one embodiment, a single image can be acquired (a single image of the object along with the projected light pattern on it). In such a case, a threshold filter is applied and local minima and maxima are determined. Such a method implies both a powerful light source (for achieving high contrast) and more computations (computing power). According to some other embodiments, a plurality of images is acquired. An optional phase modulation can be applied to highlight one or more fringes of the light pattern area.

In a preferred embodiment, two images are successively acquired and images are subtracted to identify the deformated light pattern. This solution is advantageous in some circumstances. This process enables to calculate the local reflectance of the considered object with a better accuracy. Less powerful source of light can be used (correlatively decreasing the level of danger associated with laser power). The associated methods and systems are also more robust to changes in external illumination conditions (ambient light), which can change significantly (also over time). Food elements often exhibit a variety of light reflection properties, implying the benefit of an adaptive threshold estimation with respect to local level of reflected light, as it is the case when acquiring two successive images.

Figure 12A:
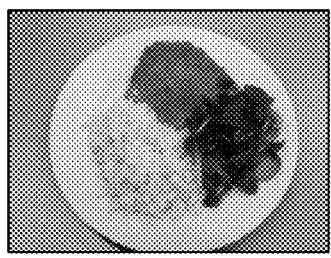
FIGS. 12A, 12B, 12C, 12D, 12E and 12F illustrate the image segmentation steps.
Figure 12B:
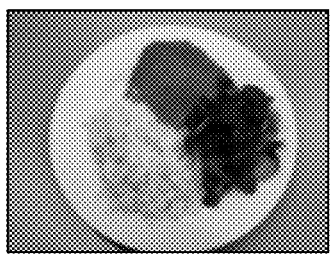
Figure 12C:
Figure 12D:
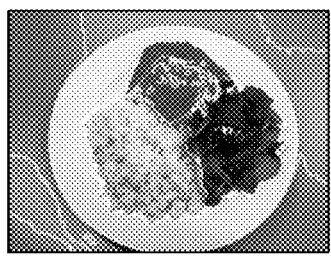

FIGS. 12A-12F illustrate the image segmentation step. Different state-of-the art image segmentation techniques can be used. In one embodiment, the segmentation algorithm consists of three steps: mean-shift filtering, region growing and region merging. FIGS. 12A-12F show several steps for the segmentation-recognition step: (a) the original image, (b) the smoothed images after mean-shift filtering, (c) the region growing result, (d) image segments after merging. First the original image (FIG. 12A) is converted to the CIELAB color space which is considered perceptually uniform. Then mean-shift filtering is applied in a pyramidal way (FIG. 12B). A Gaussian pyramid is built, the filtering is applied to the smaller scale and then the results are propagated to the larger scales. Then, a region growing method detects the initial segments based on their color homogeneity (FIG. 12C) followed by a region merging stage where segments with size smaller than a threshold are merged to the closest neighbor in terms of average color (FIG. 12D).

Figure 12E:
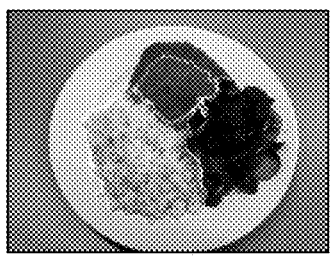
Figure 12F:
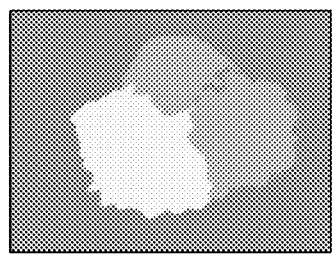

Finally the plate is detected after detecting the image edges and combining them to get the best possible ellipse with RANSAC algorithm (FIG. 12E). Segments with a large part outside the plate or sharing a big part of boarder with the plate are eliminated. At the end of the segmentation stage, some of the food items might still be over-segmented to some extent. However, if the generated regions are large enough in order to be recognized, the final segmentation result will be further improved after merging regions with the same food label (FIG. 12F).

Figure 13:
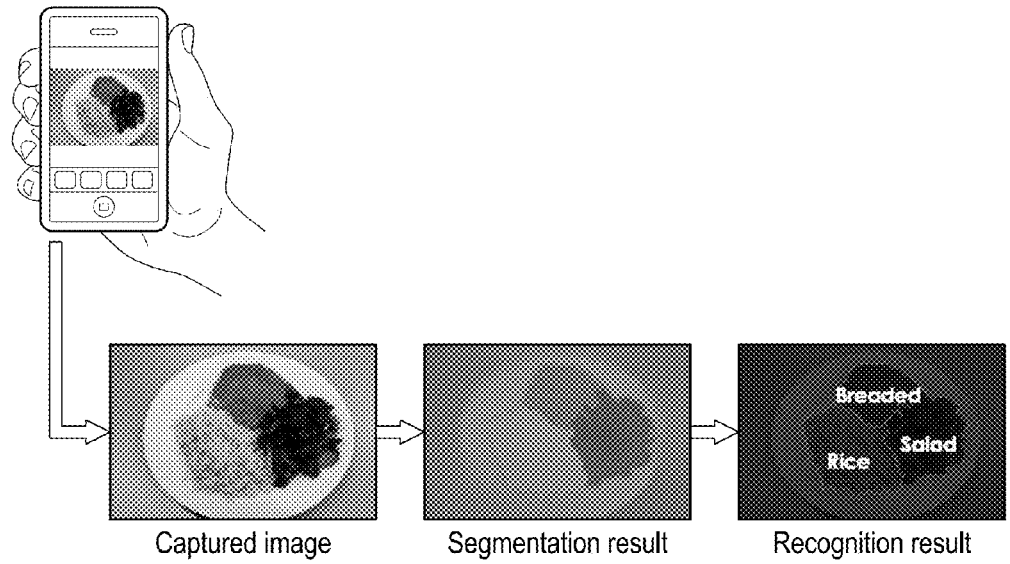
FIG. 13 illustrates the food recognition step.

FIG. 13 illustrates the food recognition step. After segmenting the meal image each of the created segments has to be recognized so a food label will be assigned to it. The food image recognition comprises two steps: image description (a set of characteristics describing the visual content of the image is extracted and quantified) and image classification (one or more classifiers assign to the image one or more classes out of a pre-defined set of food classes). Both steps require training (the system learns from the acquired knowledge) and testing (the system recognizes food types from new, unknown images). Each of the image segments produced by the previous stage is described using colour and texture features and then classified by a machine-learning based classifier into one of the pre-defined food classes. The classifier has previously been trained on a large training dataset of image patches belonging to the considered food classes. Support Vector Machines (SVM) constitute the most popular classification solution while nearest neighbor, probabilistic approaches and artificial neural networks can also be used.

In a preferred embodiment, both color and texture features can be used and then classified by a machine learning-based classifier into one of the pre-defined food classes. The classifier has previously been trained on a large training dataset of images belonging to the considered food classes. The histogram of a pre-clustered color space can be used as the color feature set. A hierarchical version of the k-means algorithm can be applied to cluster the color space created by the training set of food images, so that the most dominant food colors are determined. The use of the hierarchical k-means instead of the original k-means provides efficiency during the calculation of features since it creates a tree of hierarchical clusters with a branch factor of 2. The initial color space is split into 2 clusters and each of them is iteratively split in two until the required number of colors is reached. In some cases, a set of 512 colors can be considered as sufficiently descriptive. After clustering the image colors, their histogram is created and every histogram value is treated as a feature. For texture features, the LBP operator can be used. LBP operator is a non-parametric operator measuring the local contrast on grey scale images for efficient texture classification. The LBP operator consists of a 3×3 kernel where the center pixel is used as a threshold. Then the eight binarized neighbors are multiplied by the respective binomial weight producing an integer in the range [0 . . . 255]. Each of the 256 different 8-bit integers is considered to represent a unique texture pattern. Thus, the LBP histogram values of an image region describe its texture structure. Hence, a color and texture feature vector of 512+256=768 dimensions is created and fed to the classifier that will assign to the segment one of the predefined food classes.

Figure 14:
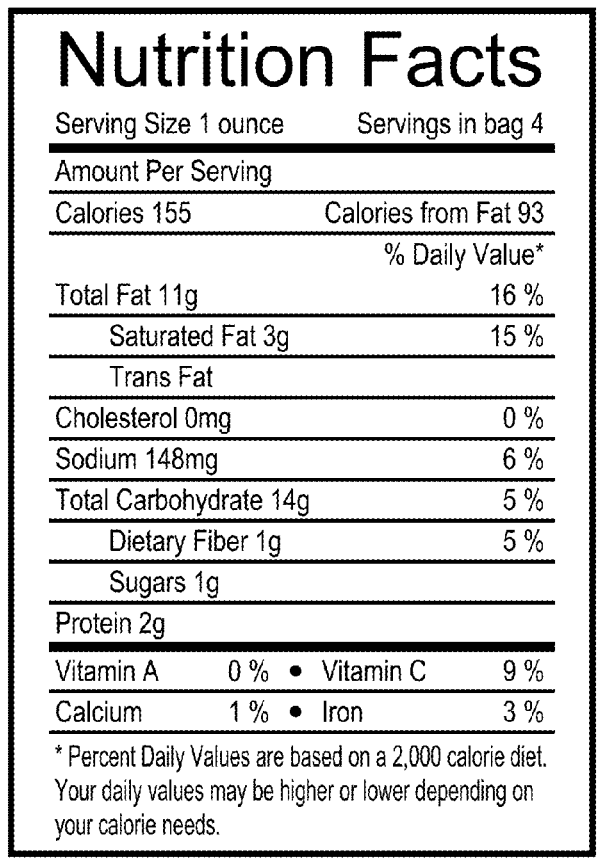
FIGS. 14 and 15 illustrate advanced bolus computations (e.g. fat content, Glycemic Index)
Figure 15:
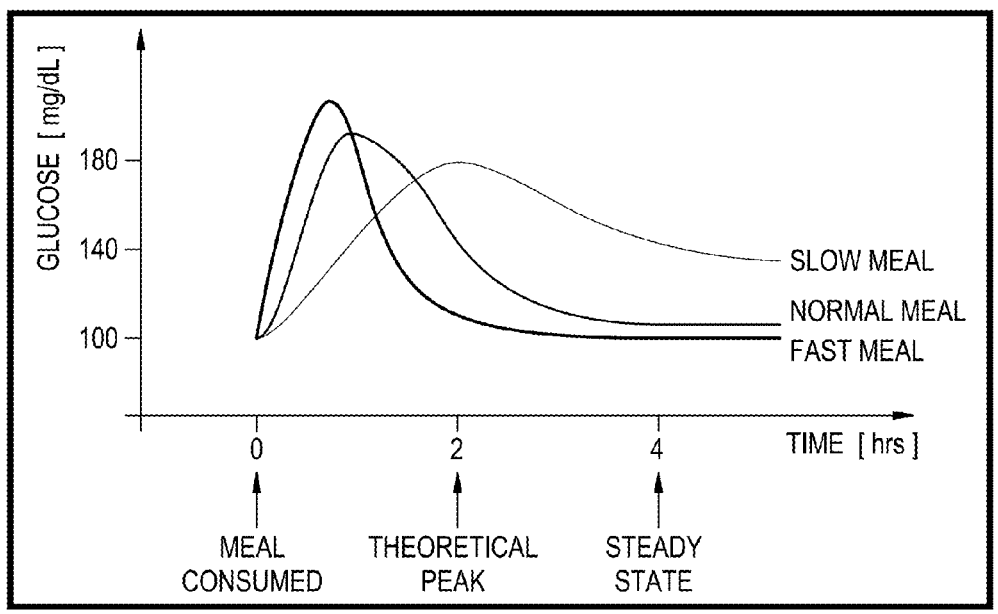

FIGS. 14 and 15 illustrate advanced bolus computations (e.g. fat content, Glycaemic Index). FIG. 14 shows an example of food labelling. Such data is generally available and can be retrieved with network connection or stored offline. Such data can be accessed by means of 2D bar code scanning. In other words, the image acquisition component can be used to capture the image of the meal, to get direct information on the food about to be consumed, but also can serve indirect purposes such as data or metadata on food, via 2D bar code scanning (or others like QR codes for example).

As described, one of the purposes of the camera is to capture images of the food about to be consumed, and to use advanced algorithms to process the images to identify both the type and the quantity of the food. In presence of an additional use of a blood glucose monitor device or of continuous glucose monitor device for example, further additional developments of the invention are enabled. By image recognition and/or by the use of such devices, further meal characteristics can be obtained and these parameters can substantially help to tailor boluses to achieve better glycaemic control.

For example, after types of food have been identified (i.e., bread, pasta, potatoes, etc.), estimates of other aspects of the meal such as the fat and protein content can be made. This information could be obtained from publicly available databases, or also from a scan of the nutrition chart of the particular meal. The camera can be used to OCR the available nutritional label if any, or data can be retrieved using RFID or (2D) bar code scanning or the like. From the fat and protein information there is the possibility of determining whether these meals are slow or fast. The terms "slow" and "fast" refer to the speed with which food causes the blood glucose value to rise and the duration over which glucose continues to go into the bloodstream. A slow meal is one that has a much longer time to attain peak glucose value as compared to a normal (lean) meal, so that its time of overall action is much greater than the standard 4 hours. Conversely, a fast meal has a much faster peak glucose value and its time of action is much faster than 4 hours. A schematic of meal speeds is provided. It is important to balance the insulin action profile with the meal activity profile to ensure proper control. A standard insulin bolus administered at the beginning of the meal, or a few minutes before the meal, is designed to handle the fast blood glucose rise caused by carbs in a fast meal. If after four hours the blood glucose is continuing to rise and the rise continues for six hours then the meal would be classified as a slow meal. In a slow meal the blood glucose rise the first hour would be relatively modest compared to that of a fast meal. Therefore for a slow meal, a standard insulin bolus may provide too much blood glucose reduction in the first two hours, perhaps causing hypoglycaemia, but not enough reduction in the 4 to 6 hour timeframe, leading to hyperglycaemia several hours after the meal.

By using the image of the meal, the system can recognize that this meal is "the same" or "substantially similar" to prior meals that the user has eaten. If the pre- and post-meal blood glucose values are available for the prior experiences with this meal, and there is a clear trend of deviation from desired glycaemic control, then adjustments for the present meal dosing and insulin can confidently be made to get an improved glycaemic response. Along these lines, the system can monitor the relative sizes of these same meals and develop a histogram of the variation in the same meals size. It is known that the size variations usually fall into a small discrete number of buckets (U.S. Pat. No. 7,941,200B2). If the system detects that such is the case, then the user's specific customized bolus sizes and delivery types could evolve from observing the meal consumption, insulin doses given and glycaemic responses of the user when consuming these "same" meals.

Monitoring the blood glucose values at 2 and 4 hours after the consumption of the meal can give a clear idea about the speed and the carbs content of the meal. Alternatively, if this system includes a continuous glucose monitoring device, then the uncertainty with respect to pre- and post-meal responses could be removed as a much more high fidelity measurement of the glucose profile is available.

An additional benefit of using this intensive approach is to determine whether the patient's therapy parameters need to be altered. If it turns out that the patient is having difficulty controlling glucose excursions only after specific meals, then it would suggest that the bolus determination would need to be addressed. If however, the patient is having consistent post-prandial excursions as verified by glucose profiles of all meals, then it would suggest that additionally, the patient therapy parameters would also need to be altered.

Further embodiments of the method handle parameters such as Glycaemic Index (GI) and/or Glycaemic Load (GL) and/or Insulin Index (II). Such values can be associated with a meal consumed by the patient. The glycaemic index, or glycaemic index, (GI) provides a measure of how quickly blood sugar levels (i.e., levels of glucose in the blood) rise after eating a particular type of food. A related measure, the glycaemic load, multiplies the glycaemic index of the food in question by the carbs content of the actual serving. The Insulin Index is a measure used to quantify the typical insulin response to various foods.

These GI, GL or II values can be given (e.g. by the restaurant or the labelling) or can be computed or estimated by image matching, or similarity search. Such values can also be directed entered by the patient, who can be invited to enter more or less meal-related information (for example, a meal speed value, corresponding to the speed at which the meal is consumed, a total glycemic index of the meal, meal size in terms of fat content, carbs content, protein content, etc). Such data also can be reconstructed from image or video analysis (for example meal speed can be derived from the video). The querying process can be configured to require a patient to enter in absolute estimates (e.g., "small") or in relative terms (e.g. "smaller than normal").

In some embodiments, steps of the method can be performed before the consumption of the meal and repeated after the meal is consumed. By subtracting estimated volumes, further carbs estimation can be handled. It may well be indeed that the user does not eat the meal completely and in such a case, subtractions operations would have to be performed. Since the food plate can be segmented into several parts (several food categories e.g. steak and potatoes), there can be associated estimations of several volumes and following an insulin bolus recommendation can be proposed, which dose correspond to food actually consumed.

FIGS. 16A-16D and 17A-17B illustrate the various options of implementation in mobile devices (e.g. mobile phones, glucometers, insulin pump controllers), as extensions or accessories or as natively embedded components. Embodiments of the invention can be implemented in various devices, in particular in medical (regulated) devices (e.g. glucometer or insulin pump controllers) or in standard and mass-market consumer electronics devices (mobile phones, tablets, computers). In a preferred embodiment, the implementation occurs in a glucometer. Such a glucometer can be provided with a light source with sufficient power and an adapted energy management profile. In such a case, for example, a second dedicated battery can be provided as source of energy for light illumination. Alternatively a dynamo system can replace or supplement the first and/or second battery to render the system more autonomous. The glucometer can further be adapted to control an insulin pump. A patient thus has a convenient solution to measure blood glucose, control the pump, estimate volume and carbs value of food, provide bolus advice and deliver insulin.

FIG. 16A shows the back view of mobile phone with an attached device according to the invention: 1) represents the objective of light source. 2) represents the aperture for mobile phone camera, 3) the light source unit. FIG. 16B shows the front view of mobile phone with attached device: 4) represents the clips for attaching the device and fixing it on mobile phone. FIG. 16C shows the scheme for attaching the device to the mobile phone: 1) represents the aperture for the camera, 2) represents the photodiode of the device.

The light source of the device can be developed based on a low intensity semiconductor laser irradiation source (FIG. 16A, 3). For example, the source can include one or several laser diodes. In case of several diodes being implemented, the irradiation of each diode is mixed with irradiation of the others and the integral output light is received by the objective (FIG. 16A, 1). In this case the irradiation wavelength of several diodes can be different. As an example, three laser diodes (commercially available lasers at low cost) with the wavelengths of 445 nm, 530 nm and 810 nm can be used. It is known that CCD cameras of all portable devices are shielded by a set of interference filters in order to reduce the noise in RGB channels. One can choose the wavelengths of the laser diodes corresponding to the maxima transfer rates of these filters. The mentioned above three wavelengths cover the spectral response of filters characteristics for most of the handy CCD cameras. One advantage of this technique is to allow to decrease the power of each source compared to the scheme with only one diode. Highlighting in different spectral ranges and integrating the corresponding signals from each RGB channel can allow to obtain high contrast of light patterns. The approach may demand more complicated optics for the objective (FIG. 16A, 1), but this might allow lower power consumption (and smaller batteries can be used). There are several solutions for wavelength mixing using a number of monochromatic light sources. For example, this can be achieved by directing the laser beam to an inner reflection prism which is installed in front of the objective (FIG. 16A, 1). The prism reflects all the light in the direction of the objective and investigated surface (e.g. food on a plate). One alternative to the prism is to use a fiber multi-wave mixing. The entrance face is attached to the diodes, while the exit face is attached to the objective (FIG. 16A, 1).

Instead of laser sources, one or more light-emitting diodes (LED) can be used. Modern versions of LEDs are available across the visible, ultraviolet, and infrared wavelengths, with very high brightness. The wavelengths band of LEDs can be wider than the one of laser diodes. Red, Blue and Green LEDs (or any LEDs in the spectral range of camera sensitivity) are advantageously used in embodiments of the invention.

Besides these LEDs of specific wavelengths, white light LEDs can be used (this kind of LEDs are typically implemented in mobile phone flash). White LEDs emit so called white pseudo colour. The irradiation spectrum of such light sources is not continuous but discrete. The spectrum is composed by a mix of blue, red and green wavelength bands, which renders the device more compact compared to the previously described laser diodes solution. In further embodiments, for better performances, additional optics can be added to compensate the diffused output of the LEDs.

Another option is to use Organic LEDs (OLEDs) instead of LEDs. Similarly, either an OLED of specific wavelength or an OLED of white light can be implemented, according to different embodiments of the invention.

Another option is to use simple and traditional white light sources like miniaturized halogen lamps (which demand more electrical power). In such an embodiment, a second battery can be used.

The light source power supply of the different described elements of the projector comprises one or more batteries and one or more voltage-to-current converters. For example, the laser diodes of the light sources according to different embodiments of the invention can be supplied with 3 button cells. Calculations indicate that the operation time on one battery while using the device three times per day (for example before each meal) can last up to 10 to 15 days. In some embodiments, the whole power supply can be placed in the same unit with laser sources and objective (FIG. 16A, 1/3). It can also be a removable or a releasable or an attachable battery.

In one embodiment, ultra-low power electronics are used, especially microcontrollers which control the operation of the external light source electrical components. For example mixed-signal microcontrollers (e.g. MSP) can be used. Such boards allow to keep devices in a hot mode (analogues to a sleeping mode for computers) and at the same time to consume extremely low current.

In another embodiment, special electrical and/or electronic switchers can be used. These cut the components of the light pattern source from the power supply during standby mode.

Long life rechargeable batteries with high energy capacity can also be used.

The objective (FIG. 16A, 1) of the device forms the light pattern and projects it onto the investigated surface (e.g. food). Projection covers the whole field of view (or field of vision or FOV) of the mobile phone camera. In one embodiment, the optical part of the objective may consist of diffraction elements that form the light pattern: For example, this optical part can be a zone plate (amplitude or phase, depending on the type of light source being implemented), and additional lenses can be mounted in order to achieve acceptable light pattern projection characteristics.

The position of the device on the mobile phone or mobile device can be variable from one measurement to another. In such a case, the aperture of light pattern projection can exceed the aperture of the mobile phone camera objective, in order to cover the field of vision of the mobile phone camera (and this in all possible positions of the attached external light source projector on the mobile device).

Alternatively, the position of the device on the mobile phone can be determined or fixed from one measurement to another. In such an embodiment, the aperture of the light pattern projection can be practically the same as the aperture of the mobile phone camera. This embodiment allows forwarding all the light from the external light source to the field of vision of the camera of the mobile phone. In the case of the fixed position the extern device is attached by matching at least some external parts of the mobile phone with at least some external parts of the device according to certain designs. For example, such position can be achieved by matching the photodiode (resp. camera aperture) of the device with the electronic flash (resp. camera objective) of the mobile phone (FIG. 16C). To set up a device to a fixed position, the photodiode and the camera aperture should be matched with the mobile phone flash and the camera objective as shown on FIG. 16C. In the fixed position of the device, the photodiode (FIG. 16C, 2) triggers the illumination of external light source depending on some mobile phone camera events.

FIG. 16D shows the mobile phone with (i) and without (ii) external passive optical element. In FIG. 16, D1 represents the output passive optical element that forms the light from the mobile phone flash into the pattern of predefined shape, FIG. 16, D2 mobile phone flash, FIG. 16, D3 mobile phone camera aperture. In this embodiment, the device comprises: an aperture for mobile phone camera (FIG. 16D, 3), aperture for the mobile phone electronic flash (D2) and (D1). The light source of mobile phone flash represents a white light LED. This gives the opportunity to use it for structured light 3D reconstruction. In this case the device represents simply the passive (or active) optical element that is matched with mobile phone flash. This optical element forms the light of the flash into the pattern of redefined shape in analogy to the previous description. As an element a phase or zone plate can be used. Besides some additional lens for concentrating the light from the flash can be installed before or after the zone plate (FIG. 16D, 1). Additional optical elements can be added here to project light pattern into the field of view of the mobile camera. In some embodiments, the aperture of the mobile phone camera may not have any optical elements. Alternatively, the device may have a variable position on mobile phone from one measurement to another. According to another embodiment, it can be placed on the mobile phone at a fixed position each time. This is achieved by matching the features between frames of the mobile phone and the external device.

The orientation of the light pattern structure inside the field of vision of the phones camera can be predefined or it can be not fixed. In both cases different algorithms are applied. The difference in algorithms is that in case of fixed orientation the scans are carried out in the direction of pattern orientation. In case of unknown orientation the scans are carried out in all directions.

Embodiments of the invention also enable the use of one single source of light, instead of two sources of light projecting specific light patterns as can be observed in known industrial systems. In particular, this single source of light can be provided as an external device with a laser irradiation unit or in simpler embodiment by reusing an existing mobile phone flash.

In some embodiments of the invention, powerful light sources (e.g. a laser) can be used to provide enough and high contrast in the reflected light, in order to detect the deformed light pattern or pattern zone. In some other and preferred embodiments, less powerful light sources are used. Dimensions of the illumination unit is decreased and energy management is optimized (this is of particular advantage if embodiments of the method are implemented in a safety-critical device, for example in the remote control of an insulin pump).

In some embodiments, extern light laser sources are used. Alternatively LED sources and/or embedded flash lights of a mobile phone can be used to project the light pattern on to the object of interest (e.g. plate with meal).

Figure 17A:
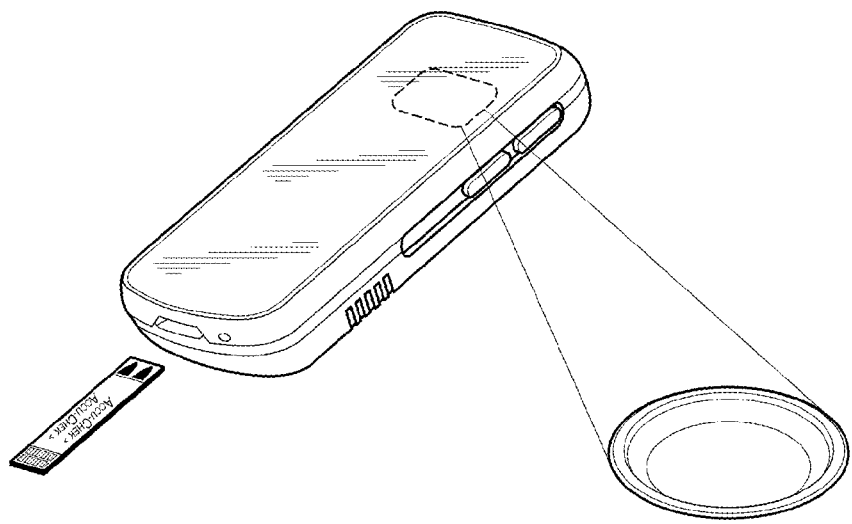
Figure 17B:
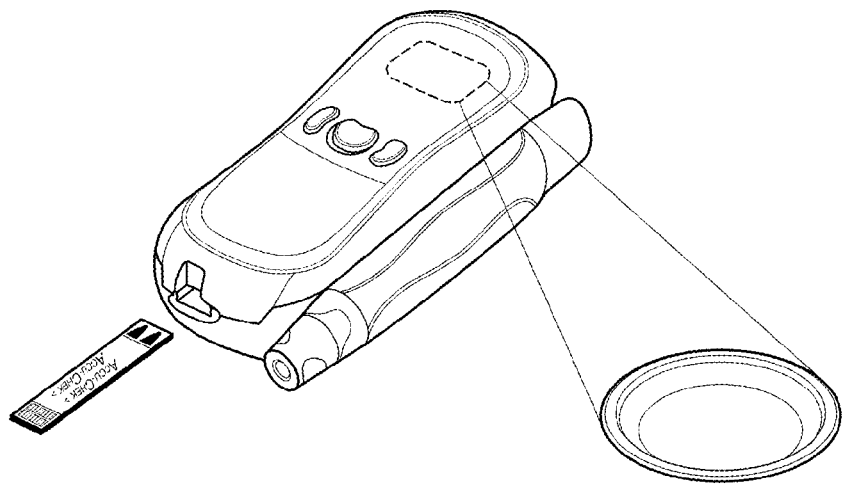

FIG. 17A and FIG. 17B illustrate other implementations of the steps according to the invention. One or more described steps and/or operations and/or the described components of the system (projector or illumination, camera, video camera etc) can be implemented in various ways. The components can be in physically separated devices for example. Or the different components can be embedded in one unique device, for example a mobile phone. Alternatively, one or more components can be implemented as extension or add-on or accessory or mountable devices. For example, the projector or light pattern projection component can be releasably attached or rigidly secured to a standard (un-modified) mobile phone. Securing or locking means (e.g. latches, hooks, anchors, magnets, adhesives, etc) can enable a fixed or moveable or releasable or attachable placement or mounting or attachment or connection of the light pattern projection component to the mobile phone. In such a case, large scale markets are enabled because unmodified phones can be used. Mobile phones are commonly provided with image acquisition capabilities and with accelerometer or motion sensors. In some other embodiments, one or more of the described systems or components and/or corresponding methods or steps or operations can be implemented in specific devices (for example in glucometers provided with image acquisition and accelerometer/motion sensor means). In some other embodiments, a remote control for an insulin pump is used. New generations of insulin pump remote controllers sometimes include a camera suitable for the capture of still images or of videos. Such acquisition means can also be used to read bar codes providing data on ingredients associated with food for example. Such remote controls or glucometers also can be provided with accelerometer. The addition of light pattern projection components or projectors or pico-projectors or lasers or lightning means, natively inside said devices or as external and connectable additional devices enables to implement aspects of the invention.

Video embodiments are now discussed.

The described methods can indeed leverage video capabilities of mobile phones, insulin pump controllers or next-generation of glucometers. The speed of image processing for image streams is limited by the refreshing frequency of the stream itself, i.e. the processing tasks can only go as fast as images are received. Higher refresh (frame) rates in mobile devices have become available. In most of the modern smart phones on the market, the frame rate is 25 frames per second (fps), while the some models support up to 30 fps. Access to the embedded camera using low level access can permit to use higher frame rates. The range of frame rates itself is limited only by the computational speed and the charge accumulation properties of the photo sensors (charge-coupled device cells or CCD). The charge-accumulation time is the necessary time for a single pixel to gather enough light and return a measurement. This minimum charge delay limits the speed of image acquisition using silicon structures to roughly 200 fps under standard light conditions (in 2013). In the described embodiments, the speed of image acquisition is in correspondence with the switch rate of the external light pattern source. In mobile phone embodiments, this rate is in relation with the mobile phone flash lamp. In some estimations, according to current available technologies, time of image acquisition speed can vary in the range of 100 to 800 milliseconds, corresponding to a fps of 1 to 10. In other words, one or more light pattern projections and one or more image acquisitions can occur in a short timeframe, for example one second.

In some embodiments, the image acquisition of the object can be carried out using the video mode of the smartphone or the mobile device. A software application triggers the light pattern projector source and at the same time launches the video recording mode. After a predefined time delay, the light source is turned off and the mobile device continues to record for a period of time equal to a certain predefined time. To optimize the computation, at least two video frames are acquired (one with and one without the projected light pattern). In some embodiments, the sequence consisting of turning projection on and off is repeated and images are continuously acquired. One or more couple of images are then selected for optimization purposes. Selection criteria comprise quantification of differences in camera positions and orientations, time delays or periods, quality of images or resulting extraction of the light pattern. In some embodiment, the selection minimizes the time delay and/or maximizes the light pattern intensity between frames. To identify the images with and without light pattern; the time of the event of light source switch on/off can be recorded, and/or the transition between frames with light pattern and those without can be detected. To recognize the images with and without light pattern on it, another optional step can occur, said sub-step consisting in comparing the histograms of subsequent images. In other optional embodiments, parameters such as time delay, frame rate or other hardware specifications can be used to discriminate between the two groups of images (with and without the projected light pattern). After the determination in the video sequence of the couple of images with and without the projected light pattern, one or more best couple of images can be determined, for example with one in each group. The best pair or couple of frames can be chosen using the minimal necessary transformation to remove shake and movement for example. After the determination of the optimal pair of frames, the other steps of the methods presently described can be carried out.

In further developments, the computations according to one or more of the described steps or embodiments of the invention can be executed continuously and optional advice (or mandatory instructions) for improving the acquisitions of images are dynamically displayed to the user (for example with arrows displayed on the screen to suggest to displace the mobile phone, to center the object on the screen, to change the angle view or the like). Image acquisitions also can be triggered automatically (for example without the user being required to press a button or to touch the screen). For example, such adaptive image acquisition advises or other embodiments of the invention can be repeated until the acquisition of images is considered as sufficient based on predefined thresholds associated with criteria comprising one or more of image quality, associated measurements of handshakes, time delays between still images or video frames, resulting computed light pattern or a combination thereof.

Embodiments of the present invention can take the form of an entirely hardware embodiment, an entirely software embodiment or an embodiment containing both hardware and software elements. Software includes but is not limited to firmware, resident software, microcode, etc. A hardware implementation may prove advantageous for processing performances. Furthermore, some embodiments of the present invention can take the form of a computer program product accessible from a computer-usable or computer-readable medium providing program code for use by or in connection with a computer or any instruction execution system. A computer-usable or computer-readable apparatus can be any apparatus that can contain, store, communicate, propagate, or transport the program for use by or in connection with the instruction execution system, apparatus, or device.

What is claimed is:
1. A system for estimating the carbs content of food on a plate (single or multiple), said system comprising instructions which when performed by a processor causes the system to operate to:

receive a first image of the food from an image acquisition component;
project a light pattern on the surface of the food with a light pattern projection component;
receive a second image of the food being highlighted with said light pattern from the image acquisition component;
identify a movement of the image acquisition component between the first and second image;
correct the first and/or the second image by an operation which compensates the movements of the image acquisition component throughout the image acquisition operation based on the artifacts to get a corrected pair of images;
subtract the first and second images of the corrected pair of images;
identify the projected light pattern on the food based upon a subtraction of the first and second corrected image; and
compute the tridimensional shape and the volume of the food given the deformations of the projected light pattern;
make segmentation and recognition of the food from the first image; and
compute the carbs content of the food based upon the volume, segmentation and recognition of food via use of nutritional databases.

2. The system of claim 1, wherein the irradiation power of the light pattern projection component is inferior to 5 mW and operates continuously, or in impulse mode with pulse frequencies between around 0.5 Hz up to 10 Hz.

3. The system of claim 1, wherein the light pattern projection component comprises one or more light sources chosen from the list comprising a low intensity semiconductor LASER diode, a LED, an organic LED (OLED), a pre-existing mobile phone flash such as a white LED or a miniaturized halogen lamp or a combination thereof with an electrical power consumption less than 0.7 W.

4. The system of claim 1, wherein the light pattern projection component comprises a light source and an optical objective adapted to form and project and/or to focus the light pattern onto the food, wherein the power density is inferior to the predefined value of 55 mWt/cm$^2$.

5. The system of claim 1, wherein the relative pose and orientation of the light pattern projection component and the image acquisition component is static during image acquisition or light pattern projection.

6. The system of claim 1, wherein the light pattern has a bright area in which the power density is inferior to 55 mWt/cm$^2$.

7. The system of claim 1, wherein the light pattern is composed of geometrical motifs such as sequences of stripes, or dots, or repetitive graphical elements or of a combination thereof.

8. The system of claim 1, wherein the light pattern is coded by color and/or phase and/or amplitude modulation.

9. The system of claim 8, wherein the coding of the light pattern is predefined and is synchronized with the image acquisition component and data processing.

10. The system of claim 1, wherein the compensation to the movements of the image acquisition component throughout the image acquisition operation is performed by processing data received from a motion sensor.

11. The system of claim 1, wherein the compensation of the movements of the image acquisition component throughout the image acquisition operation is performed by multi-view geometry methods, by projective warping, by piecewise linear, projective, or higher order warping, by deconvolution, by oriented image sharpening, or by optical flow detection before or after or in an iterative refinement process with the subtraction of the images.

12. The system of claim 1, wherein the food segmentation and recognition comprise one or more of the operations of segmenting the image, identifying color and/or texture features of segmented parts of the image and performing machine learning based classification for one or more segmented parts of the image or a combination thereof.

13. The system of claim 12, further comprising instructions which when performed by a processor causes the system to operate to estimate one or more meal characteristics of the meal captured in the first or second image by multiplying the estimated volumes of the determined food types by unitary volumetric values retrieved from a database, said database being accessed from the Internet, and/or stored locally on the device, and/or determined from food labels by using OCR and/or associated with geolocation data and/or provided by the user.

14. The system of claim 13, wherein the one or more characteristics, of the meal or of parts thereof, are one or more of carbs content, fat content, protein content, Glycemic Index (GI), Glycemic Load (GL) and/or Insulin Index (II) or a combination thereof.

15. The system of claim 14, further comprising instructions which when performed by a processor causes the system to operate to provide an insulin dose recommendation and/or a bolus profile advice based on said one or more meal characteristics.

16. The system of claim 1, wherein the system is configured to run automatically and project the light pattern via a voice command or a gesture command and/or by a touchscreen command and/or by a geo position and/or by following a predefined time schedule.

17. The system of claim 1, wherein the image acquisition component and the light pattern projection component are embedded in a mobile device such as a glucometer or an insulin pump controller provided with a test strip port or a mobile phone or a smartphone.

18. The system of claim 17 wherein the light pattern projection component is attachable to the mobile device via a clip or via insertion into an electrical contact slot in particular such as a power charge slot or a USB slot.

19. The system of claim 1, wherein the first or the second image are based upon a video frame.

20. The system of claim 1, wherein one or more operations of the system are continuously automatically repeated until the acquisition of the first and/or the second image is considered as sufficient based on predefined thresholds associated with criteria that comprises one or more of image quality, associated measurements of handshakes, time delays between still images or video frames, resulting light pattern or a combination thereof.

21. The system of claim 1, wherein the image acquisition component is embedded in a handheld device and has a sensitivity between around 0.3 up to around 3 lux.

22. The system of claim 1, wherein the light pattern projection component has an electrical power consumption between 0.05 W and 0.7 W.

23. A non-transitory computer readable medium encoded with an information processing program for use in an information processing device, said information processing program comprising instructions which when executed by a processor in the information processing device causes the information processing device to perform the operations of claim 1.

24. A non-transitory computer product comprising the non-transitory computer readable medium according to claim 23.

* * * * *